(12) United States Patent
Jamison et al.

(10) Patent No.: US 9,000,358 B2
(45) Date of Patent: *Apr. 7, 2015

(54) SYSTEMS AND METHODS FOR REAL TIME DRILLING FLUID MANAGEMENT

(71) Applicant: Halliburton Energy Services, Inc.

(72) Inventors: Dale E. Jamison, Houston, TX (US); Stephen W. Almond, North Charleston, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 151 days.

This patent is subject to a terminal disclaimer.

(21) Appl. No.: 13/713,645

(22) Filed: Dec. 13, 2012

(65) Prior Publication Data

US 2014/0166361 A1    Jun. 19, 2014

(51) Int. Cl.
*G01V 5/00* (2006.01)
*E21B 44/00* (2006.01)
*E21B 21/06* (2006.01)

(52) U.S. Cl.
CPC .............. *E21B 44/00* (2013.01); *E21B 21/065* (2013.01)

(58) Field of Classification Search
USPC ....................................... 250/253; 175/24, 40
See application file for complete search history.

(56) References Cited

U.S. PATENT DOCUMENTS

| | | |
|---|---|---|
| 5,083,622 A | 1/1992 | Hale et al. |
| 6,176,323 B1 * | 1/2001 | Weirich et al. .................. 175/40 |
| 6,198,531 B1 * | 3/2001 | Myrick et al. ................ 356/300 |
| 6,330,826 B1 | 12/2001 | Meeten |
| 6,529,276 B1 | 3/2003 | Myrick |
| 6,584,833 B1 | 7/2003 | Jamison et al. |

(Continued)

FOREIGN PATENT DOCUMENTS

| | | |
|---|---|---|
| EP | 1048819 A1 | 11/2000 |
| WO | 2011124978 A2 | 10/2011 |

(Continued)

OTHER PUBLICATIONS

International Search Report and Written Opinion for PCT/US2013/073612 dated Mar. 26, 2014.

(Continued)

*Primary Examiner* — David J Makiya
*Assistant Examiner* — Taeho Jo
(74) *Attorney, Agent, or Firm* — McDermott Will & Emery LLP; Anthony Iannitelli

(57) ABSTRACT

Disclosed are systems and methods for monitoring drilling fluid components in real time. One system includes solids control equipment fluidly coupled to a borehole and configured to receive drilling fluid from the borehole, the solids control equipment having a first optical computing device arranged adjacent the inlet and configured to optically interact with the drilling fluid as it enters the solids control equipment and thereby generate a first output signal corresponding to a characteristic of the drilling fluid, a second optical computing device arranged adjacent the outlet and configured to optically interact with the drilling fluid as it exits the solids control equipment and thereby generate a second output signal corresponding to the characteristic of the drilling fluid, and a signal processor communicably coupled to the first and second optical computing devices and configured to receive the first and second output signals and provide a resulting output signal.

21 Claims, 3 Drawing Sheets

(56) References Cited

U.S. PATENT DOCUMENTS

| | | | |
|---|---|---|---|
| 6,585,044 B2* | 7/2003 | Rester et al. | 166/250.01 |
| 7,123,844 B2 | 10/2006 | Myrick | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 8,049,881 B2 | 11/2011 | Myrick et al. | |
| 8,208,147 B2 | 6/2012 | Myrick et al. | |
| 8,575,541 B1* | 11/2013 | Jamison et al. | 250/253 |
| 2001/0036905 A1 | 11/2001 | Parlar et al. | |
| 2002/0010548 A1 | 1/2002 | Tare et al. | |
| 2002/0071121 A1 | 6/2002 | Ortyn et al. | |
| 2003/0013614 A1 | 1/2003 | Klug et al. | |
| 2003/0084717 A1 | 5/2003 | Herzhaft et al. | |
| 2003/0183393 A1 | 10/2003 | Fincher et al. | |
| 2005/0269135 A1 | 12/2005 | Swartout | |
| 2006/0142955 A1* | 6/2006 | Jones et al. | 702/32 |
| 2007/0138103 A1* | 6/2007 | Klatt | 210/695 |
| 2008/0111064 A1* | 5/2008 | Andrews et al. | 250/269.1 |
| 2008/0142211 A1* | 6/2008 | Klatt | 166/244.1 |
| 2008/0283294 A1* | 11/2008 | Colquhoun | 175/25 |
| 2009/0182693 A1 | 7/2009 | Fulton et al. | |
| 2009/0194330 A1 | 8/2009 | Gray | |
| 2009/0219539 A1 | 9/2009 | Myrick et al. | |
| 2009/0219597 A1 | 9/2009 | Myrick et al. | |
| 2010/0193249 A1 | 8/2010 | Saiz | |
| 2011/0108720 A1 | 5/2011 | Ford et al. | |
| 2011/0167901 A1 | 7/2011 | Jamison et al. | |
| 2012/0150451 A1* | 6/2012 | Skinner et al. | 702/24 |
| 2012/0211650 A1 | 8/2012 | Jones et al. | |
| 2014/0076551 A1* | 3/2014 | Pelletier et al. | 166/253.1 |
| 2014/0110105 A1* | 4/2014 | Jones et al. | 166/250.01 |
| 2014/0166871 A1* | 6/2014 | Jamison et al. | 250/254 |
| 2014/0172177 A1* | 6/2014 | Jamison et al. | 700/281 |

FOREIGN PATENT DOCUMENTS

| | | | |
|---|---|---|---|
| WO | 2014093161 A1 | 6/2014 | |
| WO | 2014093167 A1 | 6/2014 | |
| WO | 2014093432 A1 | 6/2014 | |
| WO | 2014093572 A2 | 6/2014 | |
| WO | 2014093629 A1 | 6/2014 | |

OTHER PUBLICATIONS

International Search Report and Written Opinion for PCT/US2013/074680 dated Mar. 27, 2014.

International Search Report and Written Opinion for PCT/US2013/073572 dated Mar. 25, 2014.

International Search Report and Written Opinion for PCT/US2013/074274 dated Mar. 25, 2014.

Bern et al., "Field Monitoring of Weight-Material Sag," IN: AADE Conference and Exhibition, 2010, pp. 1-11.

International Search Report and Written Opinion for PCT/US2013/074556 dated Sep. 24, 2014.

Skalle et al., Barite Segregation in Inclined Boreholes, 1999, Journal of Canadian Petroleum Technology, Special Edition 1999, vol. 38, No. 13, pp. 1-6.

* cited by examiner

SYSTEMS AND METHODS FOR REAL TIME DRILLING FLUID MANAGEMENT

BACKGROUND

The present invention relates to methods for monitoring drilling fluids and, more specifically, to methods for monitoring drilling fluid components in real time.

During the drilling of a hydrocarbon-producing well, a drilling fluid or mud is continuously circulated from the surface down to the bottom of the hole being drilled and back to the surface again. The drilling fluid serves several functions, one of them being to transport wellbore cuttings up to the surface where they are separated from the drilling fluid. Another function of the drilling fluid is to provide hydrostatic pressure on the walls of the drilled borehole so as to prevent wellbore collapse and the resulting influx of gas or liquid from the formations being drilled. For several reasons, it can be important to precisely know the characteristics and chemical composition of such drilling fluids.

Typically, the analysis of drilling fluids has been conducted off-line using laboratory analyses which require the extraction of a sample of the fluid and a subsequent controlled testing procedure usually conducted at a separate location. Depending on the analysis required, however, such an approach can take hours to days to complete, and even in the best case scenario, a job will often be completed prior to the analysis being obtained. Although off-line, retrospective analyses can be satisfactory in certain cases, but they nonetheless do not allow real-time or near real-time analysis capabilities. As a result, proactive control of drilling operations cannot take place, at least without significant process disruption occurring while awaiting the results of the analysis. Off-line, retrospective analyses can also be unsatisfactory for determining true characteristics of a drilling fluid since the characteristics of the extracted sample of the drilling fluid oftentimes changes during the lag time between collection and analysis, thereby making the properties of the sample non-indicative of the true chemical composition or characteristic.

Monitoring drilling fluids in real-time can be of considerable interest in order to determine how the drilling fluid changes over time, thereby serving as a quality control measure that may be useful in drilling fluid maintenance and drilling optimization. For instance, the viscosity of the drilling fluid is an important characteristic to monitor since it contributes to the capability of the drilling fluid to adequately transport cuttings. Clays, such as bentonite clay, are often added to the drilling fluid so as to maintain the drilled cuttings suspended within the drilling fluid as they move up the borehole. The density of the drilling fluid is another significant characteristic to monitor. The density must exhibit a certain hydrostatic pressure on the formation in order to avoid wellbore collapse, but not too large such that it would fracture the formation. Weighting materials, such as barite, are often added to the drilling fluid to make it exert as much pressure as needed to contain the formation pressures. Several other chemicals or substances may be added to the drilling fluid to give the drilling fluid the exact properties it needs to make it as easy as possible to drill the wellbore.

In order to optimize the performance of a drilling fluid during drilling operations, the physical and chemical properties of the drilling fluid and its component parts must be carefully monitored and controlled. As such, there is a continued and ongoing need for improved methods and systems that provide real time monitoring of drilling fluids.

SUMMARY OF THE INVENTION

The present invention relates to methods for monitoring drilling fluids and, more specifically, to methods for monitoring drilling fluid components in real time.

In some embodiments, a system is disclosed that may include solids control equipment fluidly coupled to a borehole and configured to receive drilling fluid from the borehole, the solids control equipment having an inlet and an outlet, a first optical computing device arranged adjacent the inlet and having a first integrated computational element configured to optically interact with the drilling fluid as it enters the solids control equipment and thereby generate a first output signal corresponding to a characteristic of the drilling fluid, a second optical computing device arranged adjacent the outlet and having a second integrated computational element configured to optically interact with the drilling fluid as it exits the solids control equipment and thereby generate a second output signal corresponding to the characteristic of the drilling fluid, and a signal processor communicably coupled to the first and second optical computing devices and configured to receive the first and second output signals and provide a resulting output signal.

In other embodiments, a method of determining a characteristic of a drilling fluid is disclosed. The method may include conveying the drilling fluid to solids control equipment fluidly coupled to a borehole, the solids control equipment having an inlet and an outlet, generating a first output signal corresponding to the characteristic of the drilling fluid with a first optical computing device arranged adjacent the inlet, the first optical computing device having a first integrated computational element configured to optically interact with the drilling fluid as it enters the solids control equipment, generating a second output signal corresponding to the characteristic of the drilling fluid with a second optical computing device arranged adjacent the outlet, the second optical computing device having a second integrated computational element configured to optically interact with the drilling fluid as it exits the solids control equipment, receiving the first and second output signals with a signal processor communicably coupled to the first and second optical computing devices, and generating a resulting output signal with the signal processor.

In yet other embodiments, a system is disclosed that may include solids control equipment fluidly coupled to a borehole and configured to receive drilling fluid from the borehole, the solids control equipment having an inlet and an outlet, an optical computing device arranged adjacent the outlet and having an integrated computational element configured to optically interact with the drilling fluid as it exits the solids control equipment and generate an output signal corresponding to a characteristic of the drilling fluid, and a signal processor communicably coupled to the optical computing device and configured to receive the output signal and provide a resulting output signal indicative of the characteristic of the drilling fluid.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is

DETAILED DESCRIPTION

Figure 1:
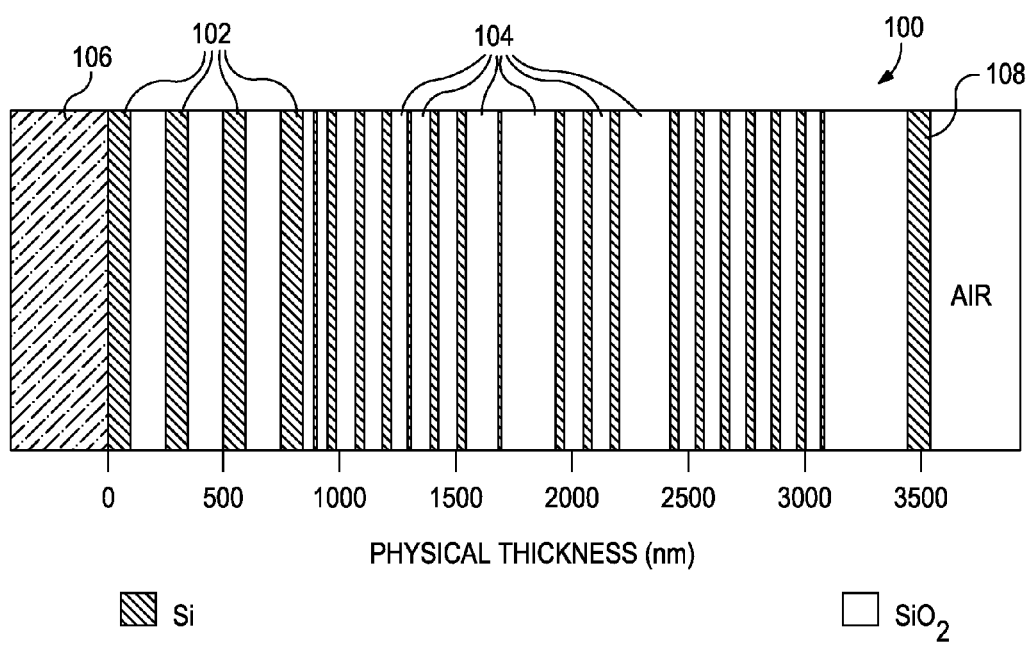
FIG. 1 illustrates an exemplary integrated computation element, according to one or more embodiments.

The present invention relates to methods for monitoring drilling fluids and, more specifically, to methods for monitoring drilling fluid components in real time.

The exemplary systems and methods described herein employ various configurations of optical computing devices, also commonly referred to as "opticoanalytical devices," for the real-time or near real-time monitoring of a fluid, such as a drilling fluid or a completion fluid. In operation, the exemplary systems and methods may be useful and otherwise advantageous in determining one or more properties or characteristics of the fluid, such as a concentration of one or more components or substances present within the fluid. The optical computing devices, which are described in more detail below, can advantageously provide real-time fluid monitoring that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, thereby allowing qualitative and/or quantitative analyses of the fluid to occur without having to extract a sample and undertake time-consuming analyses of the sample at an off-site laboratory. With the ability to undertake real-time or near real-time analyses, the exemplary systems and methods described herein may be able to provide some measure of proactive or responsive control over the fluid flow, thereby optimizing related operations.

The systems and methods disclosed herein may be suitable for use in the oil and gas industry since the described optical computing devices provide a cost-effective, rugged, and accurate means for monitoring oil/gas-related fluids, such as drilling fluids or completion fluids, in order to facilitate the efficient management of wellbore operations. The optical computing devices can be deployed various points within a flow path to monitor the fluid and the various parameter changes that may occur thereto. Depending on the location of the particular optical computing device, different types of information about the fluid can be obtained. In some cases, for example, the optical computing devices can be used to monitor changes to the fluid following circulation of the fluid into and out of a wellbore. In other embodiments, the optical computing devices can be used to monitor the fluid as a result of adding a component or substance thereto, or otherwise removing a component or substance therefrom. In yet other embodiments, the concentration of known constituent components present within the fluid may be monitored. Thus, the systems and methods described herein may be configured to monitor a flow of fluids and, more particularly, to monitor the present state of the fluid and any changes thereto with respect to any constituent components present therein.

As used herein, the term "fluid" refers to any substance that is capable of flowing, including particulate solids, liquids, gases, slurries, emulsions, powders, muds, mixtures, combinations thereof, and the like. In some embodiments, the fluid may be a drilling fluid or drilling mud, including water-based drilling fluids, oil-based drilling fluids, synthetic drilling fluids, and the like. In other embodiments, the fluid may be a completion fluid or clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "characteristic" refers to a chemical, mechanical, or physical property of a component or a substance, such as a fluid, or a component within the fluid. A characteristic of a substance may include a quantitative value of one or more chemical constituents therein or physical properties associated therewith. Such chemical constituents may be referred to herein as "analytes." Illustrative characteristics of a substance that can be monitored with the optical computing devices disclosed herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc), and the like. Moreover, the phrase "characteristic of interest of/in a fluid" may be used herein to refer to the characteristic of a substance contained in or otherwise flowing with the fluid.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "component," or variations thereof, refers to at least a portion of a substance or material of interest in the fluid to be evaluated using the optical computing devices described herein. In some embodiments, the component is the characteristic of interest, as defined above, and may include any integral constituent of the fluid flowing within the flow path. For example, the component may include compounds containing elements such as barium, calcium (e.g., calcium carbonate), carbon (e.g., graphitic resilient carbon), chlorine (e.g., chlorides), manganese, sulfur, iron, strontium, chlorine, etc., and any chemical substance that may lead to precipitation within a flow path. The component may also refer to paraffins, waxes, asphaltenes, clays (e.g., smectite, illite, kaolins, etc.), aromatics, saturates, foams, salts, particulates, hydrates, sand or other solid particles (e.g., low and high gravity solids), combinations thereof, and the like. In yet other embodiments, in terms of quantifying ionic strength, the component may include various ions, such as, but not limited to, $Ba_2^+$, $Sr_2^+$, $Fe^+$, $Fe_2^+$ (or total Fe), $Mn_2^+$, $SO_4^{2-}$, $CO_3^{2-}$, $Ca_2^+$, $Mg_2^+$, $Na^+$, $K^+$, $Cl^-$.

In other aspects, the component may refer to any substance or material added to the fluid as an additive or in order to treat the fluid or the flow path. For instance, the component may include, but is not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents and emulsifiers, de-emulsifying agents, iron control agents, proppants or other particulates, gravel, particulate diverters, salts, fluid loss control additives, gases, catalysts, clay control agents, clay stabilizers, clay inhibitors, chelating agents, corrosion inhibitors, dispersants, flocculants, base fluids (e.g., water, brines, oils), scavengers (e.g., $H_2S$ scavengers, $CO_2$ scavengers or $O_2$ scavengers), lubricants, breakers, delayed release breakers, friction reducers, bridging agents, viscosifiers, thinners, high-heat polymers, tar treatments, weighting agents or materials (e.g., barite, etc.), solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be referred to as a substance as well.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid and produce an output of electromagnetic radiation from a processing element arranged within the optical computing device. The processing element may be, for example, an integrated computational element (ICE), also known as a multivariate optical element (MOE), used in the optical computing device. The electromagnetic radiation that optically interacts with the processing element is changed so as to be readable by a detector, such that an output of the detector can be correlated to a characteristic of the fluid or a component present within the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements or multivariate optical elements), a fluid, or a component present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid or a component of the fluid.

The exemplary systems and methods described herein will include at least one optical computing device arranged along or in a flow path in order to monitor a fluid contained therein. Each optical computing device may include an electromagnetic radiation source, at least one processing element (e.g., an integrated computational element), and at least one detector arranged to receive optically interacted light from the at least one processing element or the fluid. As disclosed below, however, in at least one embodiment, the electromagnetic radiation source may be omitted and instead the electromagnetic radiation may be derived from the fluid itself. In some embodiments, the exemplary optical computing devices may be specifically configured for detecting, analyzing, and quantitatively measuring a particular characteristic of the fluid or a component present within the fluid. In other embodiments, the optical computing devices may be general purpose optical devices, with post-acquisition processing (e.g., through computer means) being used to specifically detect the characteristic of the sample.

In some embodiments, suitable structural components for the exemplary optical computing devices are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460; 12/094,465; and 13/456,467, each of which is also incorporated herein by reference in its entirety. The optical computing devices described in the foregoing patents and patent applications can perform calculations (analyses) in real-time or near real-time without the need for time-consuming sample processing. Moreover, the optical computing devices can be specifically configured to detect and analyze particular characteristics of a fluid or a component present within the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic of the fluid or a component present therein.

The optical computing devices can be configured to detect not only the composition and concentrations of a fluid or a component therein, but they also can be configured to determine physical properties and other characteristics of the fluid and/or component as well, based on an analysis of the electromagnetic radiation received from the fluid and/or component. For example, the optical computing devices can be configured to determine the concentration of an analyte and correlate the determined concentration to a characteristic of the fluid or component by using suitable processing means. As will be appreciated, the optical computing devices may be configured to detect as many characteristics of the fluid or component as desired. All that is required to accomplish the monitoring of multiple characteristics is the incorporation of suitable processing and detection means within the optical computing device for each characteristic. In some embodiments, the properties of the fluid or component can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or component will be determined.

The optical computing devices described herein utilize electromagnetic radiation to perform calculations, as opposed to the hardwired circuits of conventional electronic processors. When electromagnetic radiation interacts with a fluid, unique physical and chemical information about the fluid may be encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics or analytes within a fluid, and converting that information into a detectable output relating to one or more characteristics of the fluid or a component present within the fluid. That is, through suitable configurations of the optical computing devices, electromagnetic radiation associated with a characteristic or analyte of interest of a fluid can be separated from electromagnetic radiation associated with all other components of the fluid in order to estimate the properties of the fluid in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary ICE elements (also referred to as multivariate optical elements) is provided in *Applied Optics*, Vol. 35, pp. 5484-5492 (1996) and Vol. 29, pp. 2876-2893 (1990), which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
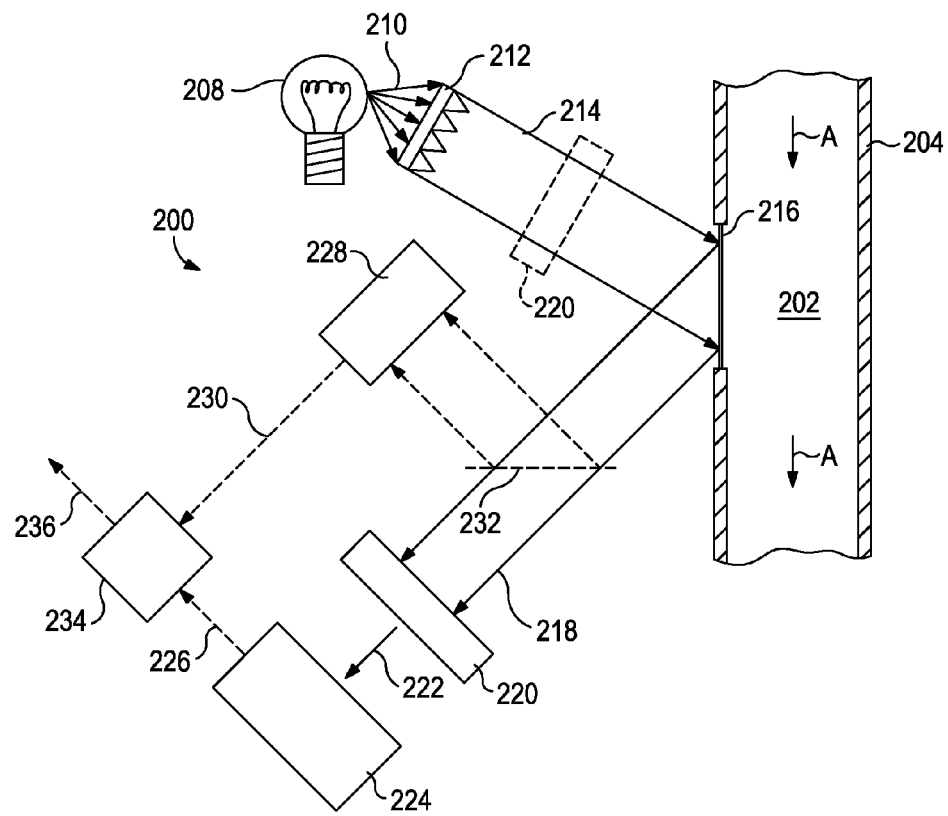
FIG. 2 illustrates an exemplary optical computing device for monitoring a fluid, according to one or more embodiments.

Referring now to FIG. 2, illustrated is an exemplary optical computing device 200 for monitoring a fluid 202, according to one or more embodiments. In the illustrated embodiment, the fluid 202 may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing in the general direction indicated by the arrows A (i.e., from upstream to downstream). As will be appreciated, however, the flow path 204 may be any other type of flow path, as generally described or otherwise defined herein. For example, the flow path 204 may be a mud pit (i.e., used for drilling fluids and the like) or any other containment or storage vessel, and the fluid 202 may not necessarily be flowing in the direction A while the fluid 202 is being monitored. As such, portions of the flow path 204 may be arranged substantially vertical, substantially horizontal, or any directional configuration therebetween, without departing from the scope of the disclosure.

The optical computing device 200 may be configured to determine a characteristic of interest in the fluid 202 or a component present within the fluid 202. In some embodiments, the device 200 may include an electromagnetic radiation source 208 configured to emit or otherwise generate electromagnetic radiation 210. The electromagnetic radiation source 208 may be any device capable of emitting or generating electromagnetic radiation, as defined herein. For example, the electromagnetic radiation source 208 may be a light bulb, a light emitting diode (LED), a laser, a blackbody, a photonic crystal, an X-Ray source, combinations thereof, or the like. In some embodiments, a lens 212 may be configured to collect or otherwise receive the electromagnetic radiation 210 and direct a beam 214 of electromagnetic radiation 210 toward the fluid 202. The lens 212 may be any type of optical device configured to transmit or otherwise convey the electromagnetic radiation 210 as desired, such as a normal lens, a Fresnel lens, a diffractive optical element, a holographic graphical element, a mirror (e.g., a focusing mirror), or a type of collimator. In other embodiments, the lens 212 may be omitted from the device 200 and the electromagnetic radiation 210 may instead be directed toward the fluid 202 directly from the electromagnetic radiation source 208.

In one or more embodiments, the device 200 may also include a sampling window 216 arranged adjacent to or otherwise in contact with the fluid 202 for detection purposes. The sampling window 216 may be made from a variety of transparent, rigid or semi-rigid materials that are configured to allow transmission of the electromagnetic radiation 210 therethrough. For example, the sampling window 216 may be made of, but is not limited to, glasses, plastics, semi-conductors, crystalline materials, polycrystalline materials, hot or cold-pressed powders, combinations thereof, or the like. After passing through the sampling window 216, the electromagnetic radiation 210 impinges upon and optically interacts with the fluid 202, including any components present within the fluid 202. As a result, optically interacted radiation 218 is generated by and reflected from the fluid 202. Those skilled in the art, however, will readily recognize that alternative variations of the device 200 may allow the optically interacted radiation 218 to be generated by being transmitted, scattered, diffracted, absorbed, emitted, or re-radiated by and/or from the fluid 202, without departing from the scope of the disclosure.

The optically interacted radiation 218 generated by the interaction with the fluid 202 may be directed to or otherwise be received by an ICE 220 arranged within the device 200. The ICE 220 may be a spectral component substantially similar to the ICE 100 described above with reference to FIG. 1. Accordingly, in operation the ICE 220 may be configured to receive the optically interacted radiation 218 and produce modified electromagnetic radiation 222 corresponding to a particular characteristic of the fluid 202. In particular, the modified electromagnetic radiation 222 is electromagnetic radiation that has optically interacted with the ICE 220, whereby an approximate mimicking of the regression vector corresponding to the characteristic of the fluid 202 is obtained.

While FIG. 2 depicts the ICE 220 as receiving reflected electromagnetic radiation from the fluid 202, the ICE 220 may be arranged at any point along the optical train of the device 200, without departing from the scope of the disclosure. For example, in one or more embodiments, the ICE 220 (as shown in dashed) may be arranged within the optical train prior to the sampling window 216 and equally obtain substantially the same results. In other embodiments, the ICE 220 may generate the modified electromagnetic radiation 222 through reflection, instead of transmission therethrough.

Moreover, while only one ICE 220 is shown in the device 200, embodiments are contemplated herein which include the use of at least two ICE components in the device 200 configured to cooperatively determine the characteristic of interest in the fluid 202. For example, two or more ICE may be arranged in series or parallel within the device 200 and configured to receive the optically interacted radiation 218 and thereby enhance sensitivities and detector limits of the device 200. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time. The two or more ICE components in any of these embodiments may be configured to be either associated or disassociated with the characteristic of interest in the fluid 202. In other embodiments, the two or more ICE may be configured to be positively or negatively correlated with the characteristic of interest in the fluid 202. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

In some embodiments, it may be desirable to monitor more than one characteristic of interest at a time using the device 200. In such embodiments, various configurations for multiple ICE components can be used, where each ICE component is configured to detect a particular and/or distinct characteristic of interest. In some embodiments, the characteristic can be analyzed sequentially using multiple ICE components that are provided a single beam of electromagnetic radiation being reflected from or transmitted through the fluid 202. In some embodiments, multiple ICE components can be arranged on a rotating disc, where the individual ICE components are only exposed to the beam of electromagnetic radiation for a short time. Advantages of this approach can include the ability to analyze multiple characteristics of the fluid 202 using a single optical computing device 200 and the opportunity to assay additional characteristics simply by adding additional ICE components to the rotating disc.

In other embodiments, multiple optical computing devices can be placed at a single location along the flow path 204, where each optical computing device contains a unique ICE that is configured to detect a particular characteristic of interest in the fluid 202. In such embodiments, a beam splitter can divert a portion of the electromagnetic radiation being reflected by, emitted from, or transmitted through the fluid 202 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 204. Likewise, multiple detection stations, each containing optical computing devices in parallel, can be placed in series for performing a similar analysis.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce an output signal 226 in real-time or near real-time in the form of a voltage (or current) that corresponds to the particular characteristic of interest in the fluid 202. The voltage returned by the detector 224 is essentially the dot product of the optical interaction of the optically interacted radiation 218 with the respective ICE 220 as a function of the concentration of the characteristic of interest of the fluid 202. As such, the output signal 226 produced by the detector 224 and the concentration of the characteristic may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 208. Undesirable radiating deviations can occur in the intensity of the electromagnetic radiation 210 due to a wide variety of reasons and potentially causing various negative effects on the device 200. These negative effects can be particularly detrimental for measurements taken over a period of time. In some embodiments, radiating deviations can occur as a result of a build-up of film or material on the sampling window 216 which has the effect of reducing the amount and quality of light ultimately reaching the first detector 224. Without proper compensation, such radiating deviations could result in false readings and the output signal 226 would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signal 226 generated by the first detector 224. As illustrated, the second detector 228 may be configured to receive a portion of the optically interacted radiation 218 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 220, 228. The signal processor 234 may be a computer including a processor and a machine-readable storage medium having instructions stored thereon, which, when executed by the processor 234, cause the optical computing device 200 to perform a number of operations, such as determining a characteristic of interest of the fluid 202. For instance, the concentration of each characteristic detected with the optical computing device 200 can be fed into an algorithm operated by the signal processor 234. The algorithm can be part of an artificial neural network configured to use the concentration of each detected characteristic in order to evaluate the overall characteristic(s) or quality of the fluid 202. Illustrative but non-limiting artificial neural networks are described in commonly owned U.S. patent application Ser. No. 11/986,763 (U.S. Patent App. Pub. No. 2009/0182693), which is incorporated herein by reference.

The signal processor 234 may also be configured to computationally combine the compensating signal 230 with the output signal 226 in order to normalize the output signal 226 in view of any radiating deviations detected by the second detector 228. Computationally combining the output and compensating signals 220, 228 may entail computing a ratio of the two signals 220, 228. For example, the concentration or magnitude of each characteristic determined using the optical computing device 200 can be fed into an algorithm run by the signal processor 234. The algorithm may be configured to make predictions on how the characteristics of the fluid 202 change if the concentrations of one or more components or additives are changed relative to one another.

In real-time or near real-time, the signal processor 234 may be configured to provide a resulting output signal 236 corresponding to a concentration of the characteristic of interest in the fluid 202. The resulting output signal 236 may be readable by an operator who can consider the results and make proper adjustments or take appropriate action, if needed, based upon the measured concentrations of components or additives in the fluid 202. In some embodiments, the resulting signal output 328 may be conveyed, either wired or wirelessly, to an operator for consideration. In other embodiments, the resulting output signal 236 may be recognized by the signal processor 234 as being within or without a predetermined or preprogrammed range of suitable operation and may alert the operator of an out of range reading so appropriate corrective action may be taken, or otherwise autonomously undertake the appropriate corrective action such that the resulting output signal 236 returns to a value within the predetermined or preprogrammed range of suitable operation.

Figure 3:
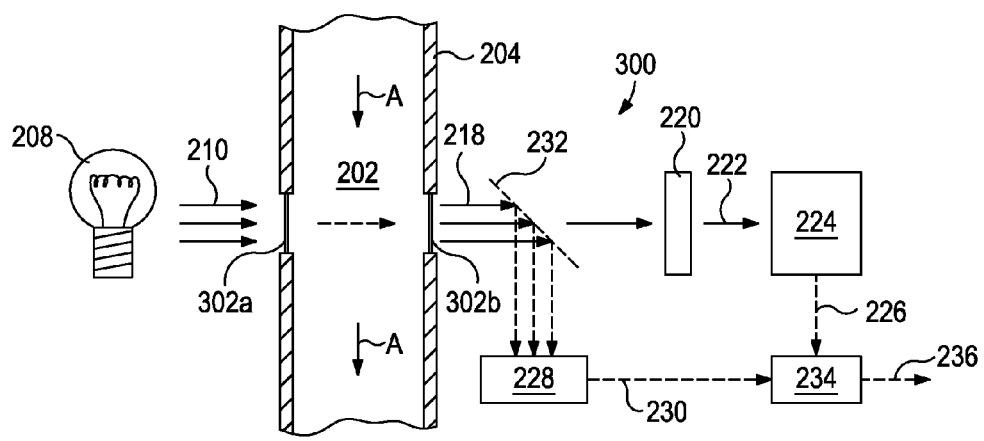
FIG. 3 illustrates another exemplary optical computing device for monitoring a fluid, according to one or more embodiments.

Referring now to FIG. 3, illustrated is another exemplary optical computing device 300 for monitoring the fluid 202, according to one or more embodiments. The optical computing device 300 may be similar in some respects to the optical computing device 200 of FIG. 2, and therefore may be best understood with reference thereto where like numerals indicate like elements that will not be described again. Again, the optical computing device 300 may be configured to determine the concentration of a characteristic of interest in the fluid 202 as contained within the flow path 204. Unlike the device 200 of FIG. 2, however, the optical computing device 300 in FIG. 3 may be configured to transmit the electromagnetic radiation 210 through the fluid 202 via a first sampling window 302a and a second sampling window 302b arranged radially-opposite the first sampling window 302a on the flow path 204. The first and second sampling windows 302a,b may be similar to the sampling window 316 described above in FIG. 2 and therefore will not be described again.

As the electromagnetic radiation 210 passes through the fluid 202 via the first and second sampling windows 302a,b, it optically interacts with the fluid 202 and optically interacted radiation 218 is subsequently directed to or otherwise received by the ICE 220 as arranged within the device 300. It is again noted that, while FIG. 3 depicts the ICE 220 as receiving the optically interacted radiation 218 as transmitted through the sampling windows 302a,b, the ICE 220 may equally be arranged at any point along the optical train of the device 300, without departing from the scope of the disclosure. For example, in one or more embodiments, the ICE 220 may be arranged within the optical train prior to the first sampling window 302a and equally obtain substantially the same results. In yet other embodiments, the ICE 220 may generate the modified electromagnetic radiation 222 through reflection, instead of transmission therethrough. Moreover, as with the device 200 of FIG. 2, embodiments are contemplated herein which include the use of at least two ICE components in the device 300 configured to cooperatively determine the characteristic of interest in the fluid 202.

The modified electromagnetic radiation 222 generated by the ICE 220 is subsequently conveyed to the detector 224 for quantification of the signal and generation of the output signal 226 which corresponds to the particular characteristic of interest in the fluid 202. The device 300 may also include the second detector 228 for detecting radiating deviations stemming from the electromagnetic radiation source 208. As illustrated, the second detector 228 may be configured to receive a portion of the optically interacted radiation 218 via the beamsplitter 232 in order to detect the radiating deviations. The output signal 226 and the compensating signal 230 may then be conveyed to or otherwise received by the signal processor 234 which may computationally combine the two signals 230, 226 and provide in real-time or near real-time the resulting output signal 236 corresponding to the concentration of the characteristic of interest in the fluid 202.

Figure 4:
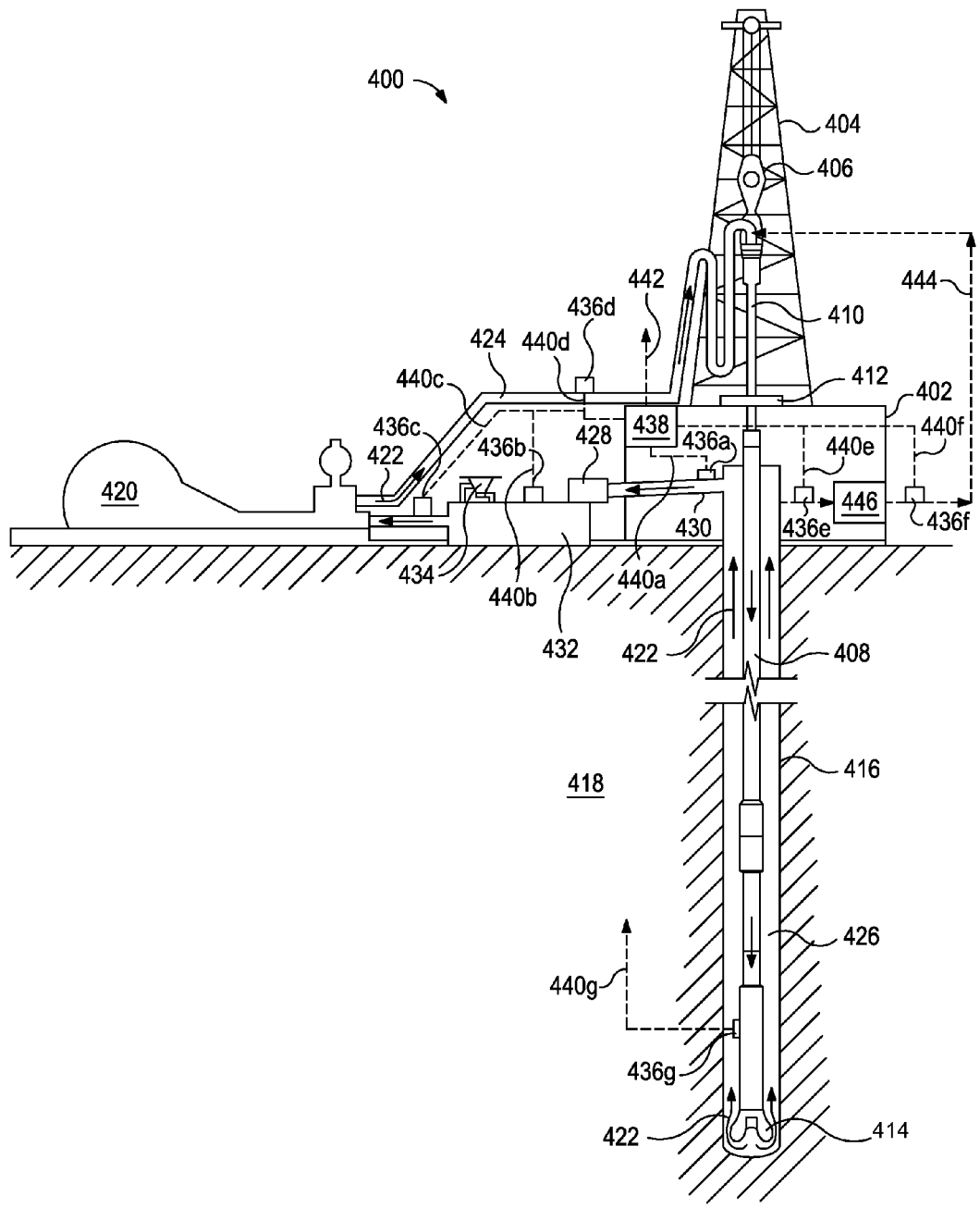
FIG. 4 illustrates an exemplary wellbore drilling assembly that may employ one or more optical computing devices for monitoring a fluid, according to one or more embodiments.

Those skilled in the art will readily appreciate the various and numerous applications that the optical computing devices 200, 300, and various alternative configurations thereof, may be suitably used with. For example, referring now to FIG. 4, illustrated is an exemplary wellbore drilling assembly 400 that may employ one or more of the optical computing devices described herein in order to monitor a drilling or clean-up fluid, according to one or more embodiments. The drilling assembly 400 may include a drilling platform 402 that supports a derrick 404 having a traveling block 406 for raising and lowering a drill string 408. A kelly 410 supports the drill string 408 as it is lowered through a rotary table 412. A drill bit 414 is attached to the distal end of the drill string 408 and is driven either by a downhole motor and/or via rotation of the drill string 408 from the well surface. As the bit 414 rotates, it creates a borehole 416 that penetrates various subterranean formations 418.

A pump 420 (e.g., a mud pump) circulates drilling fluid 422 through a feed pipe 424 and to the kelly 410, which conveys the drilling fluid 422 downhole through an interior conduit defined in the drill string 408 and through one or more orifices in the drill bit 414. The drilling fluid 422 is then circulated back to the surface via an annulus 426 defined between the drill string 408 and the walls of the borehole 416. The drilling fluid 422 serves several purposes, such as providing hydrostatic pressure to prevent formation fluids from entering into the borehole 416 and keeping the drill bit 414 cool and clean during drilling. The drilling fluid 422 also serves to carry drill cuttings and solids out of the borehole 416 and suspend the drill cuttings and solids while drilling is paused and/or when the drill bit 414 is brought in and out of the borehole 416.

At the surface, the recirculated or spent drilling fluid 422 exits the annulus 426 and may be conveyed to one or more solids control equipment 428 via an interconnecting flow line 430. In operation, the solids control equipment 428 may be configured to substantially remove the drill cuttings and solids from the drilling fluid 422 and deposit a "cleaned" drilling fluid 422 into a nearby retention pit 432 (i.e., a mud pit).

Several additives or components may be added to the drilling fluid 422 in order to maintain the drilling fluid 422 in proper working order and otherwise enhance drilling capabilities. In some embodiments, the additives and components may be added to the drilling fluid 422 via a mixing hopper 434 coupled to or otherwise in communication with the retention pit 432. In other embodiments, however, the additives and components may be added to the drilling fluid at any other location in the drilling assembly 400. In at least one embodiment, for example, there could be more than one retention pit 432, such as multiple retention pits 432 in series. Exemplary components that may be added to the drilling fluid 422 include, but are not limited to, emulsions, weighting materials, viscosifiers, thickeners, rheology modifiers, thinners, deflocculants, anionic polyelectrolytes (e.g., acrylates, polyphosphates, lignosulfonates, tannic acid derivates, etc.), high-heat polymers, clay stabilizers, clay inhibitors, tar treatments, water and other base fluids, combinations thereof, and the like. Exemplary weighting materials may include, but are not limited to, barium sulfate (i.e., $BaSO_4$ or barite), hematite, ilmenite, manganese tetraoxide, galena, calcium carbonate, or the like. Exemplary thickeners and/or rheology modifiers include, but are not limited to, xanthan gum, guar gum, glycol, carboxymethylcellulose, polyanionic cellulose (PAC), starch, or the like. Generally, exemplary components that may be added to the drilling fluid 422 will include any fluid additive, material, or component that is added to the drilling fluid 422 to change or maintain any preferred characteristic of the drilling fluid 422.

During drilling operations, and once critical concentrations of additive components have been established in the drilling fluid 422, such components may be continuously consumed or depleted from the drilling fluid 422 due primarily to being absorbed by generated drill solids. For example, components, such as emulsifiers, are commonly adsorbed onto the surfaces of drill solids which primarily include various reactive clays, such as smectite, illite, and kaolinite. As the emulsifier component is progressively depleted from the drilling fluid 422 due to losses on drill cuttings and solids, the stability of the drilling fluid 422 emulsion may be dramatically impacted. As the drilling fluid 422 emulsion becomes unstable, the rheology of the drilling fluid degrades. In extreme cases, the brine phase of the invert emulsion component can then cause water wetting of drill solids that may adversely impact drilling operations.

Component depletion may also result in higher viscosities of the drilling fluid 422, thereby requiring the pump 420 to work harder and potentially resulting in borehole 416 pressure management problems. Component depletion may also increase torque and drag on both the drill string 408 and the drill bit 414, which could lead to a stuck pipe within the borehole 416. Component depletion may further adversely affect the performance of the solids control equipment 428, such as through increased binding of solids in shaker screens. Additionally, component depletion may result in the accretion of solids onto metal surfaces, barite sag events, and the adverse exchange of ions with the surrounding formation 418.

The drilling fluid 422 may be maintained in proper working order if the depletion rate of the components is counteracted with proper fluid treatment or management. Accordingly, knowing the proper and correct treatment rate in real time may be useful in optimizing the drilling fluid 422. To accomplish this, one or more optical computing devices 436 (shown as optical computing devices 436a, 436b, 436c, and 436d) may be included in the drilling assembly 400 in order to monitor the drilling fluid 422 and/or one or more components present within the drilling fluid 422 at one or more monitoring locations. The optical computing devices 436a-d may be substantially similar to one or both of the optical computing devices 200, 300 of FIGS. 2 and 3, respectively, and therefore will not be described again in detail. In exemplary operation, the optical computing devices 436 may measure and report the real time characteristics of the drilling fluid 422, which may provide an operator with real time data useful in adjusting various drilling parameters in order to optimize drilling operations.

In some embodiments, for example, a first optical computing device 436a may be arranged to monitor the drilling fluid 422 as it is recirculated or otherwise exits out of the borehole 416. As illustrated, the first optical computing device 436a may be arranged on or otherwise coupled to the flow line 430, thereby being able to monitor the drilling fluid 422 once it exits the annulus 426. If initial concentrations or amounts of components were known prior to conveying the drilling fluid 422 into the borehole 416, the first optical computing device 436a may be useful in providing real time data indicative of how much component depletion the drilling fluid 422 underwent after being circulated through the borehole 416.

In other embodiments, a second optical computing device 436b may be arranged on or otherwise in optical communication with the retention pit 432. The second optical computing device 436b may be configured to monitor the drilling fluid 422 after it has undergone one or more treatments in the solids control equipment 428, thereby providing a real time concentration of components remaining in the drilling fluid 422. In some embodiments, the second optical computing device 436b may also be configured to monitor the drilling fluid 422 in the retention pit 432 as additional additive components are being added or otherwise mixed into the drilling fluid 422 via the mixing hopper 434. For instance, the second optical computing device 436b may be able to report to an operator when a predetermined amount or proper level of a particular additive component has been added to the drilling fluid 422 such that the performance of the drilling fluid 422 would be optimized. As will be appreciated, such real time measurement avoids unnecessarily overtreating the drilling fluid 422, thereby saving time and costs.

In yet other embodiments, a third optical computing device 436c may be arranged in the drilling assembly 400 following the retention pit 432, but prior to the mud pump 420. Alternatively, or in addition thereto, a fourth optical computing device 436d may be arranged in the drilling assembly 400 following the mud pump 420, such as being arranged at some point along the feed pipe 424. The third and/or fourth optical computing devices 436c,d may be useful in confirming whether adequate amounts or concentrations of components have been added to the drilling fluid 422 and otherwise determine whether the drilling fluid 422 is at optimal or predetermined levels for adequate drilling operations. In other embodiments, the third and/or fourth optical computing devices 436c,d may be useful in providing an initial reading of characteristics of the drilling fluid 422, including concentrations of any components found therein, prior to the drilling fluid 422 being conveyed into the borehole 416. Such an initial reading may be compared with the resulting signal provided by the first optical computing device 436a such that a determination of how much of a particular component remains in the drilling fluid 422 after circulation through the borehole 416, as briefly mentioned above.

In one or more embodiments, one or more of the optical computing devices 436a-d may be communicably coupled to a signal processor 438 and configured to convey a corresponding output signal 440a-d to the signal processor 438. The signal processor 438 may be similar to the signal processor 226 of FIGS. 2 and 3, and therefore will not be described again in detail. The signal processor 438 may employ an algorithm configured to calculate or otherwise determine any differences between any two or more of the output signals 440a-d. For example, the first output signal 440a may be indicative of a concentration of a component in the drilling fluid 422 or other characteristic of the fluid 422 at the location of the first optical computing device 436a, the second output signal 440b may be indicative of the concentration of the component or other characteristic of the fluid 422 at the location of the second optical computing device 436b, and so on. Accordingly, the signal processor 438 may be configured to determine how the concentration of the component and/or the magnitude of the characteristic of interest in the fluid 422 has changed between each monitoring location.

In real-time or near real-time, the signal processor 438 may be configured to provide a resulting output signal 442 corresponding to one or more characteristics of the fluid. In some embodiments, the resulting output signal 442 may provide a measured difference in the component and/or the magnitude of the characteristic of interest in the fluid 422. In some embodiments, the resulting output signal 442 may be conveyed, either wired or wirelessly, to an operator for consideration. In other embodiments, the resulting output signal 442 may be recognized by the signal processor 438 as being within or without a predetermined or preprogrammed range of suitable operation for the drilling fluid 422. If the resulting output signal 442 exceeds the predetermined or preprogrammed range of operation, the signal processor 438 may be configured to alert the operator so appropriate corrective action may be taken on the drilling fluid 422. Otherwise, the signal processor 438 may be configured to autonomously undertake the appropriate corrective action such that the resulting output signal 442 returns to a value within the predetermined or preprogrammed range of suitable operation. At least one corrective action that may be undertaken may include adding additional components to the drilling fluid 422 via, for example, the mixing hopper 434.

Still referring to FIG. 4, in other embodiments, one or more of the optical computing devices 436a-d may be configured to help optimize operating parameters for the solids control equipment 428. The solids control equipment 428 may include, but is not limited to, one or more of a shaker (e.g., shale shaker), a centrifuge, a hydrocyclone, a separator, a desilter, a desander, combinations thereof, and the like. In other embodiments, the solids control equipment 428 may further include one or more separators operating with magnetic fields or electric fields, without departing from the scope of the disclosure. As briefly mentioned above, the solids control equipment 428 may be configured to substantially remove the drill cuttings and other unwanted solid particulates from the drilling fluid 422, thereby depositing a "cleaned" or substantially cleaned drilling fluid 422 into the retention pit 432.

A common problem encountered with typical solids control equipment 428 is the inefficient removal of solids and other particulates. For example, when solids control equipment 428 are not properly tuned, they can sometimes pass unwanted solids or other contaminating particulates into the retention pit 432, thereby providing a less effective drilling fluid 422 to be recirculated back into the borehole 416. In other cases, un-tuned solids control equipment 428 may inadvertently remove valuable additive components or materials from the drilling fluid 422, likewise having an adverse effect on the performance of the drilling fluid 422.

To help avoid this problem, the first and second optical computing devices 436a,b may be configured to monitor the inlet and outlet of the solids control equipment 428, respectively, thereby providing an operator with a real time indication of the efficiency of the solids control equipment 428. Specifically, the first optical computing device 436a may be configured to monitor the drilling fluid 422 before or while it is introduced into the solids control equipment 428, and the second optical computing device 436b may be configured to monitor the drilling fluid 422 after it has undergone one or more processes or treatments in the solids control equipment 428 or otherwise as it is being discharged therefrom.

The output signals 440a,b derived from each optical computing device 436a,b, respectively, may provide the operator with valuable data regarding the chemical and physical conditions of the drilling fluid 422 before and after the solids control equipment 428. For instance, in some embodiments, the second output signal 440b may provide the operator with one or more characteristics of the drilling fluid 422 as it exits the solids control equipment 428. As such, the second output signal 440b may verify that particular components of interest are present within the drilling fluid 422 and thereby serve as a quality control measure for the drilling fluid 422. When concentrations of one or more components are not at their ideal levels, adjustments to the contents of the drilling fluid 422 may be undertaken in response.

In some embodiments, the output signals 440a,b may be conveyed to the signal processor 438 and a resulting output signal 442 from the signal processor 438 may provide the operator with a qualitative and/or quantitative comparison of the first and second output signals 440a,b, thereby providing valuable information as to the effectiveness of the solids control equipment 428. For instance, depending on the resulting concentrations of various additive components or other substances reported by the second optical computing device 436b, a determination may be made that the solids control equipment 428 is either operating efficiently or inefficiently. Upon being notified of ineffective or inefficient performance on the part of the solids control equipment 428, the operator may then remedy the inefficiency by altering one or more operating parameters of the solids control equipment 428. Parameters of the solids control equipment 428 that may be adjusted may include, but are not limited to, adjusting a bowl speed for a centrifuge, increasing or decreasing the screen size for a shaker, increasing or decreasing g-forces in a centrifuge or hydrocyclone, adjusting a strength of a magnetic or electrical field, etc.

Fine tuning the solids control equipment 428 will ensure that the drilling fluids 422 are maintained at proper and efficient operating levels. Moreover, when proper solids control practices are utilized, the cost to maintain the drilling fluid 422 and related equipment may decrease greatly. In some embodiments, an automated control system (not shown) may be communicably coupled to both the signal processor 438 and the solids control equipment 428. When the resulting output signal 442 (or one of the output signals 440a,b) surpasses a predetermined threshold for suitable drilling fluid 422, the automated control system may be configured to autonomously adjust the one or more operating parameters of the solids control equipment 428.

As an example, in some embodiments, the first and second optical computing devices 436a,b may be configured to monitor components and/or substances in the drilling fluid 422 such as solid particulates, clays (e.g., smectite, illite, kaolin, etc.), graphitized coke, and weighting materials (e.g., barite), which are typically removed from the drilling fluid 422 in the various solids control equipment 428. By comparing the second output signal 440b with the first output signal 440a, it may be determined as to whether the solids control equipment 428 is adequately removing the components and/or substances of interest, or whether it may be beneficial to adjust one or more parameters of the solids control equipment 428.

As another example, the first and second optical computing devices 436a,b may be configured to monitor or analyze reactive lost circulation materials (LCM) within the drilling fluid 422. As generally known in the art, LCM is solid material often added to the drilling fluid 422 to reduce and eventually prevent the flow of drilling fluid 422 into a weak or fractured downhole formation. Examples of LCM include, but are not limited to, ground peanut shells, mica, cellophane, walnut shells, calcium carbonate, plant fibers, cottonseed hulls, ground rubber, and polymeric materials. LCM is often removed from the drilling fluid 422 with the solids control equipment 428. In other embodiments, however, the solids control equipment 428 may be configured to pass a certain percentage of LCM to be recirculated back into the borehole 416. By comparing the second output signal 440b with the first output signal 440a, it may be determined as to whether the solids control equipment 428 is adequately removing the LCM from the drilling fluid 422 when desired, or whether the solids control equipment 428 is adequately allowing an appropriate amount of LCM to pass into the retention pit 432 along with the cleaned drilling fluid 422. In order to achieve optimal operation, one or more parameters of the solids control equipment 428 may be adjusted. This may also prove advantageous in providing an estimate as to how much LCM may need to be put back into the drilling fluid 422 via, for example, the mixing hopper 434 or at other location in the drilling assembly 400, as briefly mentioned above.

In some embodiments, individual optical computing devices (not shown) may be placed at the inlet and/or outlet of each of the devices used in the solids control equipment 428. For example, if applicable to the particular application, one or more optical computing devices may be placed at the inlet and/or outlet of each shaker, centrifuge, hydrocyclone, separator, desilter, and/or desander used in the solids control equipment 428. As a result, the operator may be provided with data as to the efficiency of each individual component device of the solids control equipment 428, thereby allowing for the strategic fine-tuning of each individual piece of equipment or at least the individual equipment responsible for the reported inefficiencies.

Still referring to FIG. 4, in yet other embodiments, one or more optical computing devices, as generally described herein, may be configured or otherwise arranged to monitor wellbore servicing fluids 444 and optimize associated servicing fluid reclamation equipment 446. The wellbore servicing fluid 444 may be any wellbore clean-up or completion fluid known to those skilled in the art. In some embodiments, for example, the wellbore servicing fluid 444 may be water, such as a brine or the like, or one or more spacer fluids known to those skilled in the art. The wellbore servicing fluid 444 may be, but is not limited to, municipal treated or fresh water, sea water, salt water (e.g., water containing one or more salts dissolved therein) naturally-occurring brine, a chloride-based, bromide-based, or formate-based brine containing monovalent and/or polyvalent cations, aqueous solutions, non-aqueous solutions, base oils, or combinations thereof. Examples of chloride-based brines include sodium chloride and calcium chloride. Examples of bromide-based brines include sodium bromide, calcium bromide, and zinc bromide. Examples of formate-based brines include sodium formate, potassium formate, and cesium formate.

Briefly, once drilling of the borehole 416 has been initiated, the wellbore servicing fluid 444 may be conveyed or otherwise introduced into the borehole 416 at predetermined times in order to, among other things, clean up the borehole 416 and remove wellbore filter cake. As known in the art, wellbore filter cake is a thin, slick material that can build up on the walls of the borehole 416 and serves to facilitate efficient drilling operations while simultaneously helping to prevent loss of the drilling fluid 422 into the subterranean formation 418 via "thief zones." The filter cake often includes an inorganic portion (e.g., calcium carbonate) and an organic portion (e.g., starch and xanthan). Since the filter cake essentially forms a seal on the walls of the borehole 416, hydrocarbon production from the surrounding formation 418 is substantially prevented until the filter cake is removed.

In exemplary operation, the wellbore servicing fluid 444 may be circulated through the borehole 416 in order to flush the drilling fluid 422 and associated particulate matter out of the borehole 416, while simultaneously reacting with and removing the filter cake built up on the walls of the borehole 416. In some embodiments, plugs of the wellbore servicing fluid 444 may separate individual plugs of the drilling fluid 422. In other embodiments, however, the wellbore servicing fluid 444 may be circulated through the borehole 416 at the conclusion of a drilling operation in order to perform remedial treatments in preparation for hydrocarbon production. As the wellbore servicing fluid 444 contacts the filter cake built up in the borehole 416, in some embodiments, a chemical reaction ensues and the filter cake is gradually dissolved and circulated out of the borehole 416 with either the wellbore servicing fluid 444 or the drilling fluid 422. In other embodiments, the filter cake may be solubilized, dissolved or otherwise eroded from the borehole 416.

In some embodiments, the first optical computing device 436a may be configured to monitor the drilling fluid 422 or the wellbore servicing fluid 444 as it exits the borehole 416 via the interconnecting flow line 430 and determine a concentration of a characteristic thereof, such as a chemical constituent or compound corresponding to the filter cake that may be present therein. For instance, the first optical computing device 436a may be configured to monitor the drilling fluid 422 and/or the wellbore servicing fluid 444 for concentrations of calcium carbonate, barite, clays, entrapped components, or the like.

In at least one embodiment, the output signal 440a from the first optical computing device 436a may be compared with the output signal 440d from the fourth optical computing device 436d, for example, to determine how much filter cake chemical constituent/compound was removed from the borehole 416. As the contact time with the wellbore servicing fluid 444 increases, the concentration of the filter cake chemical constituent/compound will at first increase and then gradually decrease as the filter cake is progressively reacted and/or dissolved and removed from the borehole 416. The output signal 440a from the first optical computing device 436a may provide the operator with a real time indication of how much filter cake is being dissolved or otherwise removed from the borehole 416. As a result, the operator is informed in real time as to whether the borehole 416 cleanup operation is/was successful.

In some embodiments, upon returning to the surface and exiting the borehole 416, the wellbore servicing fluid 444 may be conveyed to one or more servicing fluid reclamation equipment 446 fluidly coupled to the annulus 426. The reclamation equipment 446 may be configured to receive and rehabilitate the wellbore servicing fluid 444 in preparation for its reintroduction into the borehole 416, if desired. The reclamation equipment 446 may include one or more filters or separation devices configured to clean the wellbore servicing fluid 444. In at least one embodiment, the reclamation equipment 446 may include a diatomaceous earth filter, or the like.

In some embodiments, the drilling assembly 400 may further include a fifth optical computing device 436e and a sixth optical computing device 436f used in conjunction with the reclamation equipment 446. The fifth and sixth optical computing devices 436e,f may be substantially similar to one or both of the optical computing devices 200, 300 of FIGS. 2 and 3, respectively, and therefore will not be described again in detail. As illustrated, the fifth and sixth optical computing devices 436e,f my be used to monitor an inlet and an outlet of the reclamation equipment 446, respectively, thereby providing the operator with a real time determination of one or more characteristics of the wellbore servicing fluid 444 before and after being treated in the reclamation equipment 446. In some embodiments, for example, the characteristic of the wellbore servicing fluid 444 may include a concentration of a chemical constituent or compound corresponding to the filter cake (e.g., calcium carbonate) before and after treatment in the reclamation equipment 446. In other embodiments, the characteristic of the wellbore servicing fluid 444 may correspond to a density of the wellbore servicing fluid 444 before and after treatment in the reclamation equipment 446. In yet other embodiments, the characteristic of the wellbore servicing fluid 444 may correspond to the turbidity of the fluid 444 before and after treatment in the reclamation equipment 446.

The output signals 440e and 440f derived from each optical computing device 436e,f, respectively, may be conveyed to the signal processor 438 for processing. In some embodiments, the sixth output signal 440f may provide the operator with one or more characteristics of the wellbore servicing fluid 444 as it exits the reclamation equipment 446. As such, the sixth output signal 440f may serve as a quality control measure for the wellbore servicing fluid 444, and provide an indication to the operator whether the wellbore servicing fluid 444 is adequately rehabilitated before it is reintroduced into the borehole 416.

In some embodiments, the resulting output signal 442 from the signal processor 438 may be indicative of a difference between the fifth and sixth output signals 440e,f, thereby providing valuable information as to the effectiveness of the reclamation equipment 446 in rehabilitating the wellbore servicing fluid 444. For instance, depending on the resulting concentrations of the characteristic reported by the sixth optical computing device 436f, a determination may be made that the reclamation equipment 446 is either operating efficiently or inefficiently, and proper adjustments to the reclamation equipment 446 may be made in response thereto, if needed. As a result, optimal operating parameters for the reclamation equipment 446 may be achieved. In some embodiments, an automated control system may be communicably coupled to both the signal processor 438 and the reclamation equipment 446, and the automated control system may be configured to autonomously adjust the reclamation equipment 446 when the resulting output signal 442 (or one of the fifth and sixth output signals 440e,f) surpasses a predetermined threshold.

Still referring to FIG. 4, in other embodiments, one or more optical computing devices, as generally described herein, may be configured to monitor the drilling fluid 422 at one or more points in the drilling assembly 400 for the formation and/or concentration of gas hydrates. As generally known in the art, gas hydrates are clathrates or crystalline inclusion compounds of gas molecules in water which can form under certain temperature and pressure conditions (e.g., low temperature and high pressure) during drilling operations. Since gas hydrates consist of more than 85% water, their formation could remove significant amounts of water from the drilling fluid 422, thereby changing the fluid properties of the drilling fluid 422. This could result in salt precipitation or an increase in fluid weight.

Agglomeration of these gas hydrates in the drilling fluid 422 (or production tubing), or the formation of a solid hydrate plug, can potentially cause hazardous flow assurance problems. For instance, gas hydrates could form in the drill string 408 and associated drilling equipment, a blow-out preventer (BOP) stack (not shown), choke and kill lines (not shown), etc., which could result flow blockage, hindrance to drill string 408 movement, loss of circulation, and even abandonment of the well.

In at least one embodiment, the drilling assembly 400 may further include a seventh optical computing device 436g arranged downhole in the borehole 416 and configured to monitor the drilling fluid 422 within the annulus 426 for the presence of gas hydrates. The seventh optical computing device 436g may be substantially similar to one or both of the optical computing devices 200, 300 of FIGS. 2 and 3, respectively, and therefore will not be described again in detail. In particular, the seventh optical computing device 436g may include at least one integrated computational element (not shown) configured to detect one or more types of gas hydrates, such as methane clathrates or methane hydrates.

It should be noted that while the seventh optical computing device 436g is illustrated as a single optical computing device, it is contemplated herein to include any number of optical computing devices arranged within the borehole 416 to monitor the drilling fluid 422 for gas hydrate formation. Moreover, while the seventh optical computing device 436g is shown as being coupled at or near the drill bit 414, those skilled in the art will readily appreciate that the seventh optical computing device 436g, and any number of other optical computing devices, may be arranged at any point along the drill string 408, without departing from the scope of the disclosure.

An output signal 440g from the seventh optical computing device 436g may be indicative of a characteristic of the drilling fluid 422, such as the concentration of one or more gas hydrates within the drilling fluid 422. In some embodiments, the output signal 440g may be sent to the operator, either wired or wirelessly, and provide the operator with real time qualitative and/or quantitative data regarding the concentration of gas hydrates within the drilling fluid 422 at that particular location. In other embodiments, the output signal 440g may be conveyed to the signal processor 438 for further processing in view of or in conjunction with one or more of the other output signals 440a-f.

When the concentration of gas hydrates in the drilling fluid 422 surpasses or otherwise reaches a predetermined threshold limit, as detected or reported by the seventh optical computing device 436g, an alert or warning may be provided to the operator such that one or more corrective actions may be undertaken. Corrective actions may include adding treatment substances or compounds to the drilling fluid in order to counteract the formation of additional gas hydrates and otherwise reduce the concentration of gas hydrates within the drilling fluid 422. In other embodiments, a corrective action could include changing the salinity level of the drilling fluid.

In some embodiments, for example, a gas hydrate inhibitor may be added to the drilling fluid 422. Gas hydrate inhibitors shift the thermodynamic limit of gas hydrate formation to lower temperatures and higher pressures (i.e., thermodynamic inhibition), thereby decreasing the tendency of gas hydrate formation. Exemplary gas hydrate inhibitors include, but are not limited to salts (e.g., sodium chloride), methanol, alcohols, glycol, diethylene glycol, glycerol, polyglycerol, combinations thereof, and the like. In some embodiments, combinations of salts with water-soluble organic compounds may be used as the gas hydrate inhibitor. In other embodiments, partially-hydrolyzed polyacrylamide (PHPA) may be used as a gas hydrate inhibitor and used to links particles together to improve rheology without increased colloidal solids loading.

In some embodiments, the gas hydrate inhibitor may be added to the drilling fluid 422 via the mixing hopper 434 or at any other point in the drilling assembly 400. Following the influx of the gas hydrate inhibitor into the borehole 416, the seventh output signal 440g of the seventh optical computing device 436g may then provide the operator with the real time concentration of gas hydrates within the drilling fluid 422. If the concentration of gas hydrates fails to decrease, additional gas hydrate inhibitor may be added to the drilling fluid 422 as needed. Otherwise, if the concentration of gas hydrates returns to a manageable or "safe" operating level, the seventh output signal 440g may inform the operator that the influx of additional gas hydrate inhibitor may be maintained, reduced, or eliminated altogether. As will be appreciated, such a process of managing the addition of gas hydrate inhibitor (or any other treatment substance) to the drilling fluid 422 may be fully automated using an automated control system, as generally described above.

Accordingly, the seventh optical computing device 436g may provide an indication of whether the gas hydrate inhibitor (or any other treatment substance, for that matter) is effective or not in its intended purpose. The effectiveness of the gas hydrate inhibitor may also be determined using a before-and-after comparison of the concentration of the gas hydrate inhibitor within the drilling fluid 422. For instance, the third and/or fourth optical computing devices 436c,d may provide an initial reading of the concentration of gas hydrate inhibitor in the drilling fluid 422 prior to the drilling fluid 422 being conveyed into the borehole 416. The first optical computing device 436a may provide the concentration of the gas hydrate inhibitor after having been circulated through the borehole 416. The respective output signals output signals 440c,d and 440a may be processed in the signal processor 438, thereby providing the operator with a real time difference between the two signals, which may be indicative as to whether the gas hydrate inhibitor is properly functioning.

Those skilled in the art will readily recognize that, in one or more embodiments, electromagnetic radiation may be derived from the fluid being analyzed itself, such as the drilling fluid 422, and otherwise derived independent of any electromagnetic radiation source 208 (FIGS. 2 and 3). For example, various substances naturally radiate electromagnetic radiation that is able to optically interact with the ICE 220 (FIGS. 2 and 3). In some embodiments, for example, the fluid being analyzed may be a blackbody radiating substance configured to radiate heat that may optically interact with the ICE 220. In other embodiments, the fluid may be radioactive or chemo-luminescent and, therefore, radiate electromagnetic radiation that is able to optically interact with the ICE 220. In yet other embodiments, the electromagnetic radiation may be induced from the fluid by being acted upon mechanically, magnetically, electrically, combinations thereof, or the like. For instance, in at least one embodiment, a voltage may be placed across the fluid in order to induce the electromagnetic radiation. As a result, embodiments are contemplated herein where the electromagnetic radiation source 208 is omitted from the optical computing devices described herein.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
    solids control equipment fluidly coupled to a borehole and configured to receive drilling fluid from the borehole, the solids control equipment having an inlet and an outlet;
    a first optical computing device arranged adjacent the inlet and having a first integrated computational element configured to optically interact with the drilling fluid as it enters the solids control equipment and thereby generate a first output signal corresponding to a first measurement of a characteristic of the drilling fluid;
    a second optical computing device arranged adjacent the outlet and having a second integrated computational element configured to optically interact with the drilling fluid as it exits the solids control equipment and thereby generate a second output signal corresponding to a second measurement of the characteristic of the drilling fluid; and
    a signal processor communicably coupled to the first and second optical computing devices and configured to receive the first and second output signals and provide a resulting output signal, the signal processor further configured to normalize one of the first or second output signals with a compensating signal indicative of an intensity deviation of an electromagnetic radiation used for optically interacting at least one of the first or second integrated computational elements with the drilling fluid.

2. The system of claim 1, wherein the solids control equipment is at least one of a shaker, a centrifuge, a hydrocyclone, a separator, a desilter, a desander, and a separator that operates using magnetic or electrical fields.

3. The system of claim 1, wherein the resulting output signal is indicative of how the characteristic of the drilling fluid changes between the inlet and outlet.

4. The system of claim 1, wherein the characteristic of the drilling fluid is a concentration of a substance in the drilling fluid.

5. The system of claim 4, wherein the substance comprises a substance selected from the group consisting of solid particulates, clays, weighting materials, and lost circulation materials.

6. The system of claim 1, further comprising an automated control system communicably coupled to the signal processor and configured to adjust one or more operating parameters of the solids control equipment in response to the resulting output signal.

7. The system of claim 1, further comprising:
a first detector configured to receive the optically interacted light from the first integrated computational element and generate the first output signal; and
a second detector configured to receive the optically interacted light from the second integrated computational element and generate the second output signal.

8. The system of claim 1, further comprising:
a first electromagnetic radiation source arranged in the first optical computing device and being configured to emit electromagnetic radiation that optically interacts with the drilling fluid prior to entering the solids control equipment; and
a second electromagnetic radiation source arranged in the second optical computing device and being configured to emit electromagnetic radiation that optically interacts with the drilling fluid after exiting the solids control equipment.

9. A method of determining a characteristic of a drilling fluid, comprising:
conveying the drilling fluid to solids control equipment fluidly coupled to a borehole, the solids control equipment having an inlet and an outlet;
generating a first output signal corresponding to a first measurement of the characteristic of the drilling fluid made with a first optical computing device arranged adjacent the inlet, the first optical computing device having a first integrated computational element configured to optically interact with the drilling fluid as it enters the solids control equipment;
generating a second output signal corresponding to a second measurement of the characteristic of the drilling fluid made with a second optical computing device arranged adjacent the outlet, the second optical computing device having a second integrated computational element configured to optically interact with the drilling fluid as it exits the solids control equipment;
receiving the first and second output signals with a signal processor communicably coupled to the first and second optical computing devices;
receiving a compensating signal from at least one of the first or second optical computing devices, the compensating signal indicative of an intensity deviation of an electromagnetic radiation used for optically interacting at least one of the first or second integrated computational elements with the drilling fluid; and
generating a resulting output signal with the signal processor, wherein the generating the resulting output signal comprises normalizing one of the first or second output signals with the compensating signal.

10. The method of claim 9, wherein generating the resulting output signal comprises determining how the characteristic of the drilling fluid changed between the inlet and the outlet of the solids control equipment.

11. The method of claim 9, wherein the characteristic of the drilling fluid is a concentration of a substance in the drilling fluid.

12. The method of claim 11, wherein the substance comprises a substance selected from the group consisting of solid particulates, clays, weighting materials, and lost circulation materials.

13. The method of claim 9, further comprising conveying the resulting output signal to a user for consideration.

14. The method of claim 9, further comprising adjusting one or more operating parameters of the solids control equipment in response to the resulting output signal.

15. The method of claim 14, wherein the one or more operating parameters of the solids control equipment are adjusted by an automated control system communicably coupled to the signal processor.

16. The method of claim 9, wherein the second output signal is a concentration of the characteristic of the drilling fluid as measured by the second optical computing device, the method further comprising using the second output signal as a quality control measure for the drilling fluid.

17. A system, comprising:
solids control equipment fluidly coupled to a borehole and configured to receive drilling fluid from the borehole, the solids control equipment having an inlet and an outlet;
an optical computing device arranged adjacent the outlet and having an integrated computational element configured to optically interact with the drilling fluid as it exits the solids control equipment and generate an output signal corresponding to a characteristic of the drilling fluid; and
a signal processor communicably coupled to the optical computing device and configured to receive the output signal and provide a resulting output signal indicative of the characteristic of the drilling fluid, and further configured to normalize the output signal according to a compensating signal indicative of an intensity deviation of an electromagnetic radiation used for optically interacting at least one of the first or second integrated computational elements with the drilling fluid.

18. The system of claim 17, wherein the solids control equipment is at least one of a shaker, a centrifuge, a hydrocyclone, a separator, a desilter, a desander, and a separator that operates using magnetic or electrical fields.

19. The system of claim 17, wherein the characteristic of the drilling fluid is a concentration of a substance in the drilling fluid as the drilling fluid exits the solids control equipment.

20. The system of claim 19, wherein the substance comprises a substance selected from the group consisting of solid particulates, clays, weighting materials, and lost circulation materials.

21. The system of claim 17, wherein the resulting output signal is used as a quality control measure for the drilling fluid.

* * * * *